United States Patent [19]

King et al.

[11] 3,943,937

[45] Mar. 16, 1976

[54] GAS ABSORBING IMPLANTABLE ELECTRICAL MEDICAL DEVICE

[75] Inventors: Wendell L. King, Isanti; Kenneth B. Stokes, Minneapolis, both of Minn.

[73] Assignee: Medtronic, Inc., Minneapolis, Minn.

[22] Filed: July 5, 1974

[21] Appl. No.: 485,952

[52] U.S. Cl. .............................. 128/419 P; 136/179
[51] Int. Cl.² .......................................... A61N 1/36
[58] Field of Search .... 128/1 R, 405, 419 C, 419 E, 128/419 P, 419 PS, 419 R, 421, 422; 136/177, 179

[56] References Cited
UNITED STATES PATENTS

| | | | |
|---|---|---|---|
| 3,033,911 | 5/1962 | Duddy | 136/177 |
| 3,159,508 | 12/1964 | Chreitzberg | 136/179 |
| 3,690,325 | 9/1972 | Kenny | 128/419 P |
| 3,842,842 | 10/1974 | Kenny et al. | 128/419 P |

Primary Examiner—William E. Kamm
Attorney, Agent, or Firm—Schroeder Siegfried Ryan & Vidas

[57] ABSTRACT

An implantable electrically actuated medical device having gas storage characteristics in which the device includes one or more electrochemical cells and an operative electric circuitry mounted in a metallic container, all of which are positioned in a mounting member made of a material which is highly permeable with respect to hydrogen gas, relatively impervious to liquid and which bonds well with an epoxy resin encapsulant coating over the device. The mounting member may be foamed as it is molded to provide voids therein for storage of gas or the recesses in which the electrochemical cells are mounted may be supplied with sponge-like pads for absorbing excess gas until it can permeate through the encapsulant to reduce pressure build-up within the device and prevent cracking of the casing.

5 Claims, 4 Drawing Figures

GAS ABSORBING IMPLANTABLE ELECTRICAL MEDICAL DEVICE

Our invention relates to an implantable electrically actuated medical device, such as a cardiac pacer, and more particularly to an improved device of this type which has gas storage characteristics.

Devices of this type are normally energized and powered from either separate or self-contained electrochemical cells or batteries which tend to deplete chemically and with such depletion generate a hydrogen gas. Inasmuch as devices of this type are normally encapsulated with an epoxy resin which is highly impermeable to the hydrogen gas, the encapsulated structure under conditions of cell deterioration will occasion substantial internal pressure build-up with the risk of an explosion or splitting of the encapsulating casing.

The present invention is directed to an improved device of this type in which means are provided in the construction of the device and beneath the encapsulation to absorb any hydrogen gas evolving from the electrochemical cells energizing the same. In the present invention, the components of the electrically operated medical device are positioned in a mounting structure which is generally made of a material which is highly permeable to the hydrogen gas relative to the encapsulating material or epoxy resin the material of such a structure being foamed to provide spaces or voids therein to provide a reservoir space for the gas, releasing or reducing internal pressure until the gas may be permeated through the encapsulation. An alternate arrangement is provided in which the mounting structure for the cells and electrical device includes a separate sponge-like material for the same purpose.

It is the principle object of this invention to provide an improved electrically actuated medical device having gas absorption characteristics.

Another object of this invention is to provide an improved electrically actuated medical device of the implantable type in which the internal construction permits absorption of hydrogen gas generated by power-sources or other electrochemical cells which have a gas byproduct.

These and other objects of this invention will become apparent from the reading of the attached description, together with the drawings, wherein.

Figure 1:
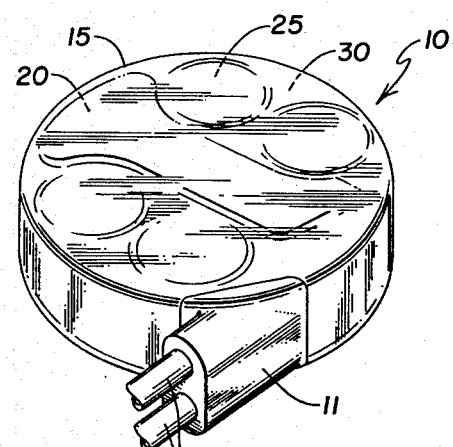
FIG. 1 is a perspective view of the improved implantable electrically actuated medical device.

Our improved electrically operated and implantable medical device is shown in perspective in FIG. 1 simulating a cardiac pacer. Although the invention shown is herein in connection with an implantable cardiac pacer, it will be understood that it may take varying forms within the scope of the invention including other implantable medical devices.

Figure 2:
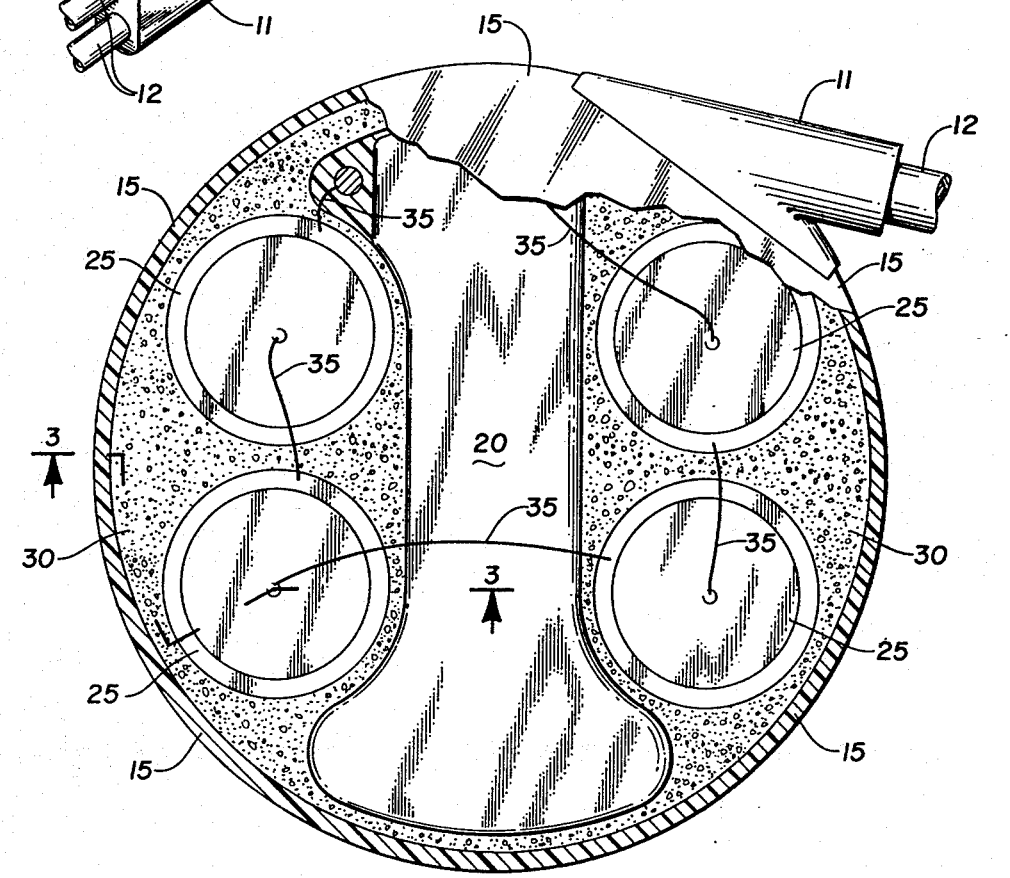
FIG. 2 is a plan view of the device of FIG. 1 with parts broken away to show the arrangement of parts therein.

As shown in FIGS. 1 and 2, the implantable medical device includes an encapsulation 15 of an epoxy resin covering a plurality of electrochemical cells 25 typically of the alkaline zinc-mercury type which are positioned in a mounting member 30 along with a sealed can or housing for the electronic circuitry of the device indicated generally at 20. The cells 25 are interconnected to one another and to the input terminals of the device, as indicated by the conductors 35, and the implantable device has a coupling member extending through the encapsulation as indicated at 11 with suitable output leads 12 extending therefrom and to electrodes (not shown) or other apparatus associated with the device. The details of the electrochemical cells and the electronic circuitry are omitted for simplicity since they form no part of the present invention. The cells are of the type which generate a gas, such as hydrogen upon depletion. The epoxy resin covering or encapsulation provides a relatively liquid tight seal for the device of a material which is biocompatible and liquid impervious. Where the voids liquid light or liquid impervious are used herein, it is meant that the resin will not pass fluid in liquid form while recognizing that the plastic resin will transmit small amounts of vapor. The epoxy resin covering is also relatively impermeable to any hydrogen gas generated in the cells. Such generation of gas takes place with cell depletion with the gas being vented from a suitable vent port, indicated at 40, in the base of the cell and to some degree through the cell seal spacing the cell electrodes. Because the epoxy resin material is relatively impermeable to gas any sudden release of the same will create a pressure build-up within the encapsulation which may cause fracture or explosion of the same.

Figure 3:
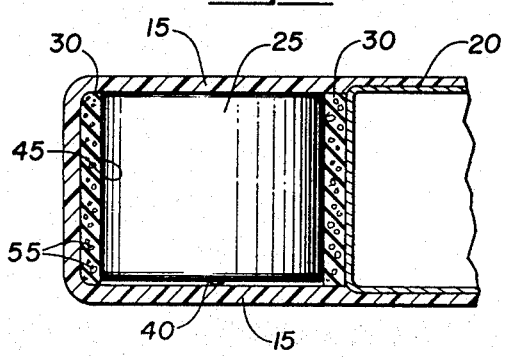
FIG. 3 is a sectional view of the device of FIG. 2 taken along the lines 3—3 therein and with parts broken away; and, FIG. 4 is a sectional view similar to FIG. 3 of the device showing an alternate embodiment of the invention.

In the present invention, as indicated in FIG. 3, the mounting member 30 is formed of a highly hydrogen permeable plastic which may advantageously be a polyphenyleneoxide/polystyrene material commercially available under the trademark "NORYL" as manufactured by the General Electric Company. The mounting member or spacer 30 has recesses 45 therein in which the cells and electronic circuit can 20 are positioned. The mounting member provides for location of the parts and rigidity to the package to support the encapsulation which bonds well with the mounting material to seal the same. In the present invention, the material forming and mounting member is constructed of a structural foam providing voids or spaces in the mounting member, as indicated at 55, which act as a reservoir for the hydrogen gas when released from the cells through the vent extremity 45 thereof. The mounting material of polyphenyleneoxide/polystyrene is of considerably higher permeability to hydrogen gas than is the epoxy resin and is also biocompatible with body fluids. The release of gas from the cells is absorbed in the voids or foamed spacer member to provide a very slow development of pressure within the casing permitting diffusion of the gas or release of the same through the encapsulant material or epoxy resin gradually without an excessive pressure build-up from the same.

Figure 4:
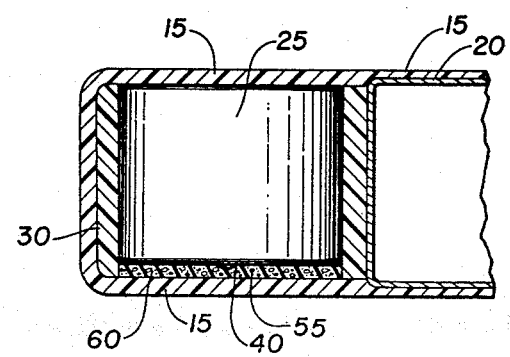

As an alternate embodiment of this invention, as indicated in FIG. 4, the recesses 45 in the mounting member beneath the electrochemical cells or batteries may have a thin layer of sponge material 60 positioned therein which sponge material will face the vent 40 extremity of the cells to increase the free volume of gas to occupy within the mounting member and the encapsulation. The use of the sponge material with voids therein to store the gas permits the gradual release of the same and prevents pressure build-up within the encapsulated device. In this embodiment, the spacer or mounting member may be made solid rather than foamed with reliance on the sponge-like pads positioned adjacent and in contact with the vent ends of the electrochemical cells within the recesses of the device providing the storage space for the excess to reduce pressure build-up within the encapsulant and permit diffusion of the same through the mounting member and the encapsulant.

In the description given above, the foamed material has been given as polyphenyleneoxide/polystyrene plastic. This material while suitable to purposes of the invention, is not the only usable plastic. What is required is that the plastic be foamable to produce a structural foam body that holds the assembly in position, provides a temporary storage space for evolved hydrogen and has good hydrogen permeability relative to the epoxy encapsulant. It also should bond readily to the epoxy.

In considering this invention, it should be remembered that the present disclosure is illustrative only and the scope of the invention should be determined by the appended claims.

What we claim is:

1. An implantable electrically operated medical device comprising, at least one electrochemical generating cell, an electrically powered actuating device connected to the cell and energized therefrom, a mounting member being formed of a plastic material having good permeability to hydrogen relative to epoxy resin and having recesses therein mounting said cell and said device in said recesses, a covering of epoxy resin material positioned over and encapsulating said mounting member with the cell and device therein, and means including said mounting member providing a space for absorption and storage of hydrogen gas from said cell, said epoxy resin being biocompatable with and impervious to body fluids and bonding well with the plastic material of the mounting member.

2. The implantable electrically operated medical device of claim 1 in which the means including said mounting member providing a space are voids distributed in the mounting member through the creation of bubbles in the plastic material.

3. The implantable electrically operated medical device of claim 1 in which a means including the mounting member is a pad of sponge-like and gas absorbing material included with the mounting member.

4. The implantable electrically operated medical device of claim 3 in which a pad of sponge-like material is positioned in a recess mounting the electrochemical cell and at a vent extremity of the same.

5. The implantable electrically operated medical device of claim 1 in which plastic material of the mounting member is a foamed polyphenyleneoxide/polystyrene material.

* * * * *